United States Patent
Whisenant et al.

(10) Patent No.: US 10,493,191 B2
(45) Date of Patent: Dec. 3, 2019

(54) VENTRICULAR ASSIST DEVICE AND RELATED METHODS

(71) Applicant: Coherex Medical, Inc., Salt Lake City, UT (US)

(72) Inventors: Brian K. Whisenant, Salt Lake City, UT (US); Richard J. Linder, Sandy, UT (US); Scott D. Miles, Sandy, UT (US); David L. Stott, Providence, UT (US); Randall K. Jones, Murray, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

(21) Appl. No.: 16/178,412

(22) Filed: Nov. 1, 2018

(65) Prior Publication Data

US 2019/0070349 A1    Mar. 7, 2019

Related U.S. Application Data

(60) Continuation of application No. 15/243,805, filed on Aug. 22, 2016, now Pat. No. 10,124,100, which is a
(Continued)

(51) Int. Cl.
*A61M 1/12* (2006.01)
*A61M 1/10* (2006.01)
(Continued)

(52) U.S. Cl.
CPC ....... *A61M 1/122* (2014.02); *A61B 17/00234* (2013.01); *A61B 17/11* (2013.01); *A61M 1/10* (2013.01); *A61M 1/12* (2013.01); *A61M 1/125* (2014.02); *A61M 27/002* (2013.01); *A61B 2017/00243* (2013.01); *A61B 2017/00252* (2013.01); *A61B 2017/00292* (2013.01); *A61B 2017/1107* (2013.01); *A61B 2017/1135* (2013.01); *A61B 2017/3425* (2013.01); *A61B 2017/3484* (2013.01); *A61B 2017/3488* (2013.01); *A61F 2/06* (2013.01); *A61F 2/064* (2013.01); *A61M 1/101* (2013.01);
(Continued)

(58) Field of Classification Search
CPC .... A61M 1/122; A61M 1/101; A61M 1/1086; A61M 1/125
USPC .......................................................... 600/16
See application file for complete search history.

(56) References Cited

U.S. PATENT DOCUMENTS 5,190,528 A    3/1993    Fonger et al.
5,928,132 A    7/1999    Leschinsky
(Continued)

FOREIGN PATENT DOCUMENTS

WO    WO 00/37139       6/2000
WO    WO 2005/037345    4/2005
(Continued)

*Primary Examiner* — Amanda K Hulbert
*Assistant Examiner* — Philip C Edwards
(74) *Attorney, Agent, or Firm* — David L. Stott

(57) ABSTRACT

A method and system are provided for percutaneously gaining access to oxygenated blood with one or more anastomosis devices and pumping such oxygenated blood directly to the aorta adjacent to the right atrium or left atrium via a VAD system. In one embodiment, a VAD system can be implanted with open surgery.

16 Claims, 16 Drawing Sheets

Related U.S. Application Data continuation of application No. 14/500,811, filed on Sep. 29, 2014, now Pat. No. 9,421,310, which is a continuation of application No. 14/034,332, filed on Sep. 23, 2013, now Pat. No. 8,845,509, which is a division of application No. 12/938,030, filed on Nov. 2, 2010, now Pat. No. 8,540,616, which is a continuation-in-part of application No. 12/435,056, filed on May 5, 2009, now Pat. No. 8,235,885.

(60) Provisional application No. 61/257,754, filed on Nov. 3, 2009, provisional application No. 61/050,568, filed on May 5, 2008.

(51) Int. Cl.
| | | |
|---|---|---|
| *A61M 27/00* | (2006.01) | |
| *A61B 17/00* | (2006.01) | |
| *A61B 17/11* | (2006.01) | |
| *A61B 17/34* | (2006.01) | |
| *A61F 2/06* | (2013.01) | |

(52) U.S. Cl.
CPC ......... *A61M 1/1008* (2014.02); *A61M 1/1086* (2013.01); *A61M 1/127* (2013.01); *A61M 2205/32* (2013.01); *A61M 2205/3334* (2013.01)

(56) References Cited

U.S. PATENT DOCUMENTS

| | | |
|---|---|---|
| 6,090,096 A | 7/2000 | St. Goar et al. |
| 6,306,116 B1 | 10/2001 | Hancock |
| 6,344,022 B1 | 2/2002 | Jarvik |
| 6,926,662 B1 * | 8/2005 | Aboul-Hosn ....... A61M 1/3621 600/16 |
| 6,974,436 B1 | 12/2005 | Aboul-Hosn et al. |
| 2003/0176760 A1 | 9/2003 | El Oakley et al. |
| 2004/0102674 A1 | 5/2004 | Zadini et al. |
| 2004/0191116 A1 | 9/2004 | Jarvik et al. |
| 2004/0027287 A1 | 12/2004 | Onaka et al. |
| 2004/0249431 A1 | 12/2004 | Ransbury et al. |
| 2005/0165344 A1 | 7/2005 | Dobak, III |
| 2005/0187425 A1 * | 8/2005 | Alferness ............... A61M 1/127 600/16 |
| 2005/0251187 A1 | 11/2005 | Beane et al. |
| 2005/0256540 A1 | 11/2005 | Silver et al. |
| 2006/0155158 A1 * | 7/2006 | Aboul-Hosn ........... A61M 1/12 600/16 |
| 2006/0270893 A1 | 11/2006 | Billing et al. |
| 2007/0161845 A1 | 7/2007 | Magovern et al. |
| 2007/0293724 A1 | 12/2007 | Saadat et al. |
| 2009/0088597 A1 | 4/2009 | Frazier et al. |
| 2009/0112050 A1 | 4/2009 | Farnan et al. |

FOREIGN PATENT DOCUMENTS

| | | |
|---|---|---|
| WO | WO 2007/047212 | 4/2007 |
| WO | WO 2008/027869 | 3/2008 |

\* cited by examiner

VENTRICULAR ASSIST DEVICE AND RELATED METHODS

CROSS-REFERENCE TO RELATED APPLICATIONS

The present application is a continuation application of U.S. Non-Provisional patent application Ser. No. 15/243, 805, filed Aug. 22, 2016, which is a continuation application of U.S. Non-Provisional patent application Ser. No. 14/500, 811, filed Sep. 29, 2014, now U.S. Pat. No. 9,421,310, issued on Aug. 23, 2016, which is a continuation application of U.S. Non-Provisional patent application Ser. No. 14/034, 332, filed Sep. 23, 2013, now U.S. Pat. No. 8,845,509, issued Sep. 30, 2014, which is a divisional of U.S. Non-Provisional patent application Ser. No. 12/938,030, filed Nov. 2, 2010, entitled VENTRICULAR ASSIST DEVICE AND RELATED METHODS, now U.S. Pat. No. 8,540,616, issued on Sep. 24, 2013, which claims the benefit of U.S. Provisional Patent Application Ser. No. 61/257,754, filed Nov. 3, 2009, entitled VENTRICULAR ASSIST DEVICE AND RELATED METHODS, the disclosures of which are incorporated by reference herein in their entirety. Further, the above-noted U.S. Non-Provisional patent application Ser. No. 12/938,030 is a continuation-in-part of U.S. Non-Provisional patent application Ser. No. 12/436,056, filed May 5, 2009, entitled VENTRICULAR ASSIST DEVICE AND RELATED METHODS, now U.S. Pat. No. 8,235,885, issued on Aug. 7, 2012, which claims the benefit of U.S. Provisional Patent Application Ser. No. 61/050,568, filed May 5, 2008, entitled METHOD AND APPARATUS FOR CONNECTING A VENTRICULAR ASSIST DEVICE TO A HEART, the disclosures of which are incorporated by reference herein in their entirety.

TECHNICAL FIELD

The present invention relates generally to methods, apparatus and systems for connecting a ventricular assist device to a heart. More specifically, the present invention relates to methods and apparatus for percutaneously connecting a ventricular assist device to a heart as well as surgically connecting a ventricular assist device.

BACKGROUND

There are several instances when it is desirable to provide assistance to the heart in performing its function of pumping blood through the body. For example, when the heart has been arrested to perform a surgical procedure and then started again after the procedure, the heart conventionally needs assistance for some period of time until it has developed sufficient strength and overcomes the trauma of being arrested. In other examples, a patient may experience some form of cardiac failure such that the heart requires more permanent assistance.

One type of assist device is known as a ventricular assist device (VAD) which helps pump blood through the body when, for example, a ventricle lacks sufficient strength to perform this function. More specifically, left ventricular assist devices (LVADs) have been used for some time to assist in the flow of oxygenated blood through the body.

An LVAD may be implemented through a procedure so as to couple, either directly, or indirectly, the device to the left atrium or left ventricle of the heart. Many of such procedures require open-heart surgery and are, therefore, extremely invasive and are particularly burdensome on patients that are already experiencing extreme health problems. Other procedures may be performed, and devices implemented, in a less invasive manner, but they may still pose a considerable risk to a patient or may be impractical for longer term use.

As such, it would be advantageous for a less invasive and less life threatening methods for providing an LVAD system or apparatus to a patient experiencing circulatory challenges. Further, in many instances, it would be advantageous for such system, apparatus and method to be implanted for the long-term use and benefit of the patient.

BRIEF SUMMARY OF THE INVENTION

The present invention is directed to methods and systems for percutaneously connecting a ventricular assist device to a heart as well as to components used in such methods and systems. In some embodiments, the present invention is directed to methods and systems for connecting a ventricular assist device to a heart as well as to components used in such methods and systems employing open surgery.

In accordance with one embodiment of the present invention, a system to assist the left ventricle of a heart is provided. The system includes a first anastomosis device, a second anastomosis device, a flow path including at least one conduit and a pumping device. The first anastomosis device is configured to be coupled to a septum between a right atrium and a left atrium of the heart. The second anastomosis device is configured to be coupled between the right atrium of the heart and the aorta. The flow path that includes at least one conduit is configured to be positioned within the right atrium of the heart and is configured to flow oxygenated blood from the left atrium, through the first anastomosis device, to the second anastomosis device and directly into the aorta. The pumping device is operatively coupled to the at least one conduit.

In one embodiment, a filament is coupled to the pumping device and extends therefrom. The filament can be configured to exhibit sufficient length to extend from the pumping device through a vascular system of a patient and out an access point, to be exposed on the patient. Such a filament can include multiple wires configured to facilitate power and control of the pumping device via a controller.

In another embodiment, the at least one conduit is configured to be positioned exclusively within the right atrium of the heart. In another embodiment, the pumping device is coupled at or between the first anastomosis device and the second anastomosis device. In another embodiment, the pumping device is configured to be positioned in the right atrium of the heart to pump arterial blood directly to the aorta. In still another embodiment, the first anastomosis device is shaped and configured to be substantially flush with a wall of the septum.

In accordance with another embodiment of the present invention, a method for percutaneously connecting a ventricular assist device to a heart is provided. The method includes accessing a right atrium of the heart with a catheter; puncturing a septum of the heart to access oxygenated blood in a left atrium of the heart; implanting a first anastomosis device in the septum; puncturing the heart to access an aortic artery, where the aortic artery is adjacent to the heart; implanting a second anastomosis device to maintain access to the aortic artery; and connecting a pumping device and at least one conduit, the at least one conduit positioned in the right atrium to extend between the first anastomosis device and the second anastomosis device, the pumping device configured to pump arterial blood from the left atrium to the aortic artery.

In one embodiment, the method includes withdrawing the catheter from the heart over a filament extending from the pumping device. Further, in another embodiment, the method includes securing the filament, coupled to the pumping device, to a controller to be exposed on the patient. Even further, in another embodiment, the method includes snaring the filament with a snare device and pulling the filament through the superior vena cava to be exposed at an upper region of the patient to interconnect with the controller.

In another embodiment, the method includes accessing the right atrium of the heart with a second catheter to perform the puncturing the heart to access the aortic artery. Further, in another embodiment, the method includes accessing the right atrium of the heart with a third catheter to perform the connecting the pumping device and the at least one conduit between the first anastomosis device and the second anastomosis device.

In another embodiment, the method of implanting includes the implanting the first anastomosis device and the implanting the second anastomosis device with a common catheter. Further, the method can include the connecting the pump and the at least one conduit with a common catheter.

In accordance with another embodiment of the present invention, a method for connecting a ventricular assist device to a heart is provided. The method includes; puncturing the heart to access an aortic artery downstream of an aortic valve and directly adjacent to the right atrium or left atrium of the heart; and implanting an anastomosis device in tissue of the heart, the anastomosis device providing a conduit for arterial blood to flow from a left atrium of the heart to the aortic artery, the arterial blood flowing to the aortic artery via a pumping device operatively coupled to the anastomosis device.

In one embodiment, the method includes percutaneously accessing the heart with a catheter. In another embodiment, the method includes connecting the ventricular assist device directly through open surgery.

In one embodiment, the puncturing includes performing an anastomosis between the left atrium and the right atrium; and performing an anastomosis between the right atrium and the aortic artery. In another embodiment, the puncturing includes performing an anastomosis between the left atrium and the aortic artery. In still another embodiment, the implanting includes implanting a pumping device adjacent to the anastomosis device.

In accordance with another embodiment of the present invention, a method for connecting a ventricular assist device to assist a heart is provided. The method includes performing an anastomosis in an aortic artery; implanting a first anastomosis device in the anastomosis in the aortic artery; performing an anastomosis in a pulmonary vein; implanting a second anastomosis device in the anastomosis in the pulmonary vein; extending conduit between the first anastomosis device and the second anastomosis device with a pumping device positioned at or between the first anastomosis device and the second anastomosis device for pumping oxygenated blood from the pulmonary vein to the aortic artery; extending a filament subcutaneously from the pumping device to be exposed at an upper region of a body of a patient; and interconnecting an exposed portion of the filament to a controller to power and control the pumping device.

In accordance with another embodiment of the present invention, a system to assist a left ventricle of heart is provided. The system includes an anastomosis device and a pumping device. The anastomosis device is configured to be coupled to and extend between a left atrium and the aortic artery, the anastomosis device including a flow path configured to flow oxygenated blood from the left atrium directly into the aortic artery. The pumping device is directly coupled to the anastomosis device and is configured to pump the oxygenated blood through the anastomosis device directly into the aortic artery.

In one embodiment, the system includes a filament extending from the pumping device and configured to extend through a vasculature system of a patient and out an access point to be exposed on the patient. In another embodiment, the system includes a controller configured to be operatively coupled to the filament and configured to control the pumping device. The filament may include wires configured to facilitate power and control of the pumping device.

In another embodiment, the anastomosis device includes conduit extending between the left atrium and the aortic artery. In another embodiment, the anastomosis device includes a protruding portion configured to protrude from the interior wall of the left atrium with multiple openings formed in the protruding portion of the anastomosis device. In still another embodiment, the anastomosis device includes at least one shoulder configured to maintain the anastomosis device between the left atrium and the aortic artery.

In accordance with another embodiment of the present invention, a system to assist a left ventricle of a heart is provided. The system includes a first anastomosis device, a second anastomosis device a flow path and a pumping device. The first anastomosis device is configured to be coupled to an aortic artery adjacent the heart. The second anastomosis device is configured to be coupled to a pulmonary vein adjacent the heart. The flow path includes at least one conduit configured to be positioned and connected between the first anastomosis device and the second anastomosis device. The pumping device is operatively coupled to the at least one conduit.

In one embodiment, the pumping device is directly coupled to the first anastomosis device and configured to pull blood from the pulmonary vein to the aortic artery. In another embodiment, the system includes a third anastomosis device configured to be coupled to another pulmonary vein adjacent the heart. In still another embodiment, the at least one conduit includes a first end, a second end and a third end, the first end being coupled to the first anastomosis device, the second end being coupled to the second anastomosis device and the third end being coupled to the third anastomosis device.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
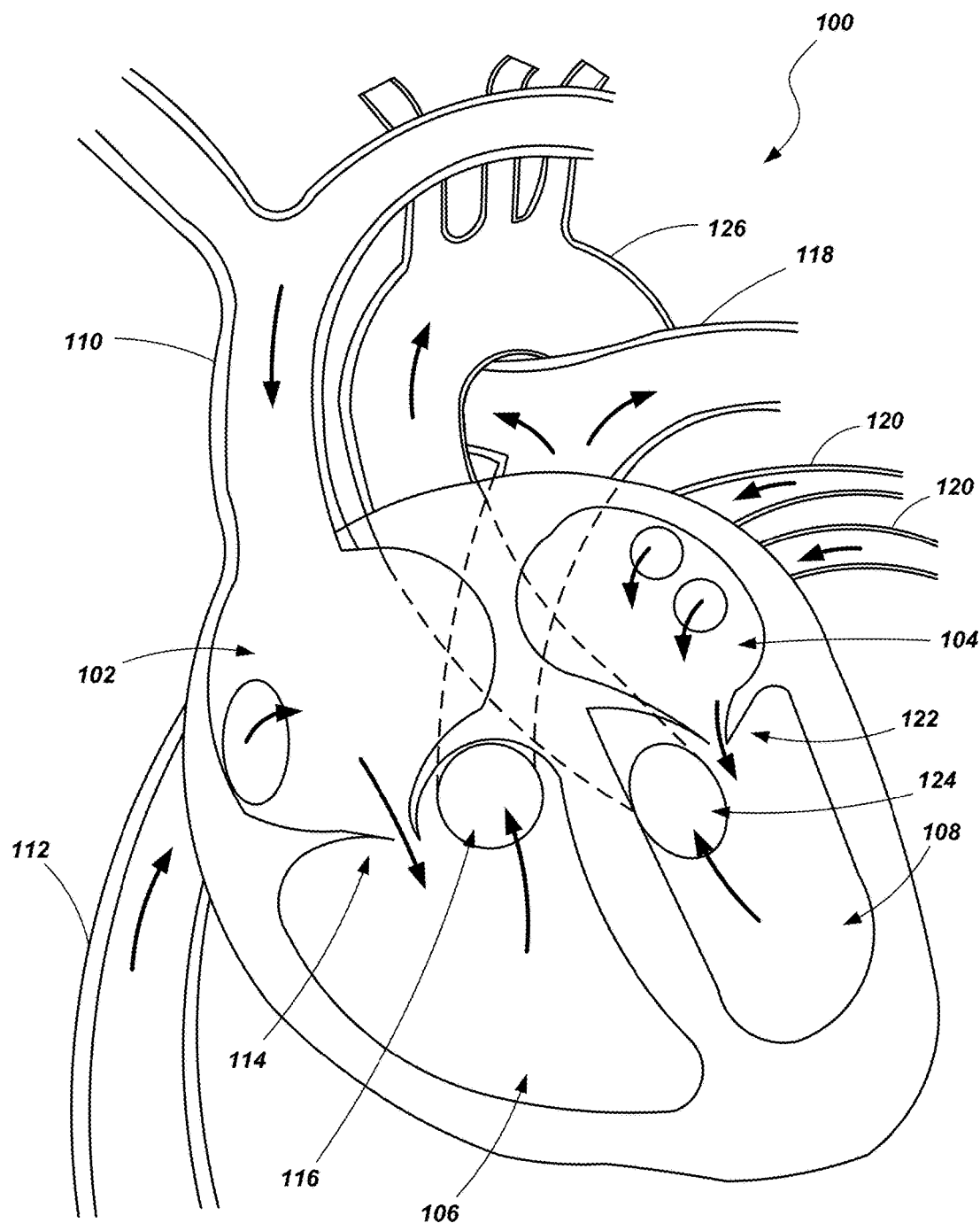
FIG. 1 is a simplified, cross-sectional view of a human heart and certain blood vessels associated therewith.

Embodiments of the present invention are directed to methods, apparatus and systems for percutaneously connecting a ventricular assist device to a heart. Referring first to FIG. 1, a simplified, cross-sectional view of a human heart 100 is shown for purposes of context in describing embodiments of the present invention.

The human heart 100 includes several chambers that effect blood flow through the human body. These chambers include the right atrium 102, the left atrium 104, the right ventricle 106 and the left ventricle 108. The right atrium 102 receives unoxygenated blood from veins including the superior vena cava 110 and the inferior vena cava 112. It will be appreciated by those of ordinary skill in the art that the superior vena cava 110 receives blood from various veins such as the jugular veins, the subclavian veins, and numerous others. Likewise, those of ordinary skill in the art will appreciate that the inferior vena cava 112 receives blood from various veins such as the femoral veins.

Blood passes from the right atrium 102 to the right ventricle 106 through a tricuspid valve 114. Upon contraction of the right ventricle 106, blood is passed through the pulmonary valve 116 and through the pulmonary artery 118 to the lungs (not shown). The lungs oxygenate the blood which then returns to the heart 100, via pulmonary veins 120, to the left atrium 104.

Oxygenated blood passes through the mitral valve 122 and into the left ventricle 108. Upon contraction of the left ventricle 108, oxygenated blood passes through the aortic valve 124 and into the aorta 126. The aorta passes the blood to a network of arteries including the brachiocephalic artery, subclavian arteries, axillary arteries, brachial arteries, the carotid arteries, the femoral arteries and many others as will be appreciated by those of skill in the art.

As noted above, there are various situations where the heart needs some assistance in pumping blood through its network of arteries and veins. One type of assist device is a ventricular assist device (VAD) wherein assistance is provided to one of the ventricles by helping to pump the blood normally pumped upon contraction of such ventricles. More specifically, a left ventricular assist device (LVAD) helps to pump oxygenated blood to the aorta or associated arteries. The following description is directed more particularly to examples of LVADs, although various acts and apparatus described herein will find use in other devices, systems and methods.

Figure 2:
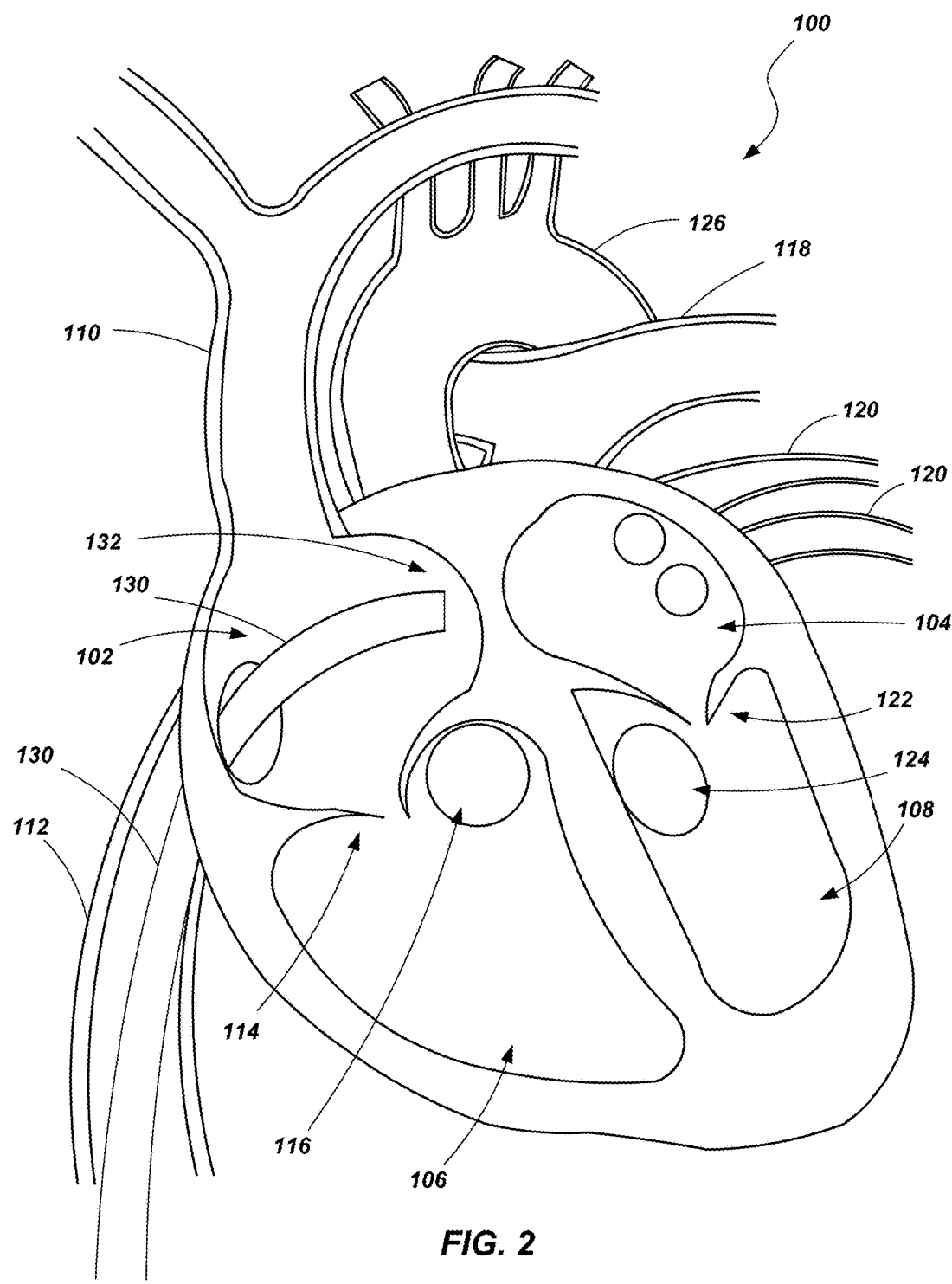
FIGS. 2 through 11 are simplified, cross-sectional views of a human heart at different stages of a procedure according to embodiments of the present invention and utilizing various devices and components in accordance with certain embodiments of the present invention.

Referring to FIG. 2, a catheter 130 is directed to the right atrium 102 through the inferior vena cava 112, such as by a femoral vein. The catheter 130 may be guided using the assistance of fluoroscopic imaging, ultrasound imaging or both or any other suitable imaging technique. Such access of the right atrium 102 via a femoral vein is well known to those of ordinary skill in the art and is not described in further detail herein. The catheter 130 may include known components, such as a dilator and stylet, and may be used to perform a procedure such as puncturing the septum 132, the septum separating the right atrium 102 from the left atrium 104. By puncturing the septum 132, access to oxygenated blood in the left atrium 104 may be obtained through the right atrium 102.

Figure 3:
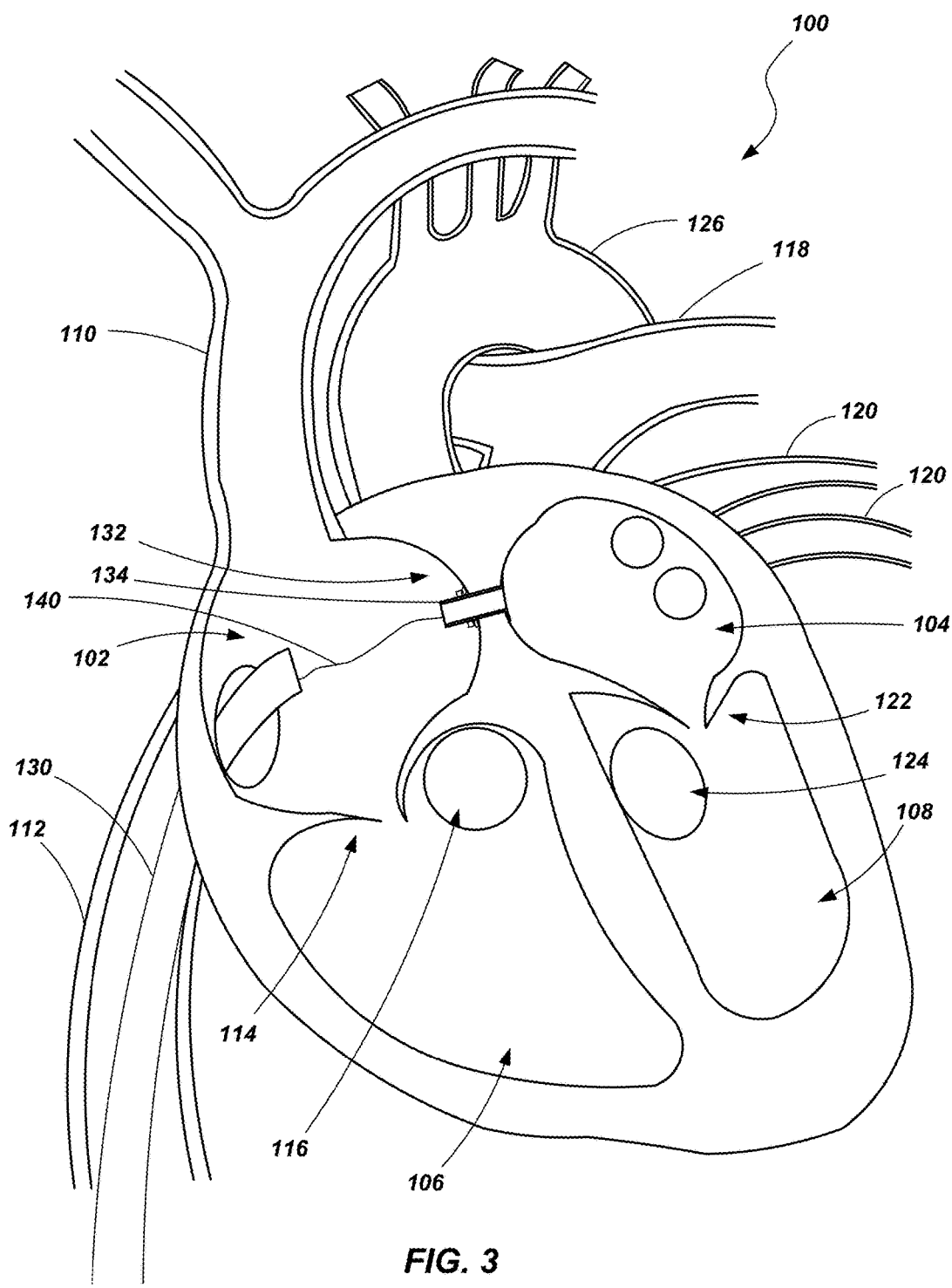
Figure 12:
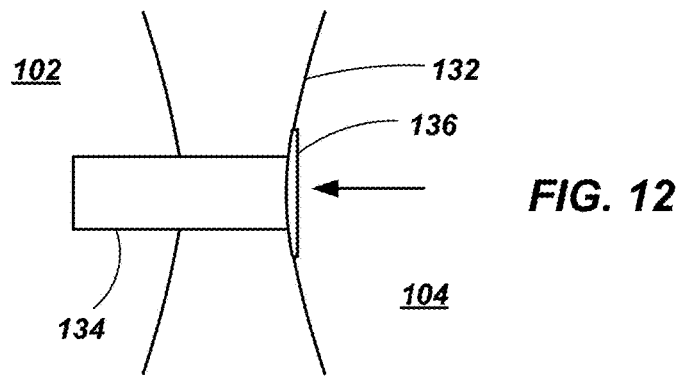
FIG. 12 is a component utilized in association with a ventricular assist device in accordance with an embodiment of the present invention.

As shown in FIG. 3, an anastomosis device 134 may be inserted through and coupled to the septum 132. In one embodiment, the anastomosis device 134 may be configured such that it extends into the right atrium 102 but does not substantially extend into the left atrium 104. For example, as seen in FIG. 12, the anastomosis device 134 may have a small shoulder 136 or other feature or structure that abuts the left atrial side of the septum 132 to create a relatively smooth or flush transition along the septum wall and into a passage or flow channel defined by the anastomosis device 134. By keeping the anastomosis device 134 substantially out of the left atrium 104, and by having a smooth transition from the septum wall into the passage of the anastomosis device 134, the potential of thrombosis formation is reduced, the amount of pressure required to draw oxygenated blood from the left atrium 104 is also reduced and there is less likelihood of hemolysis (red blood cell damage).

Figure 13:
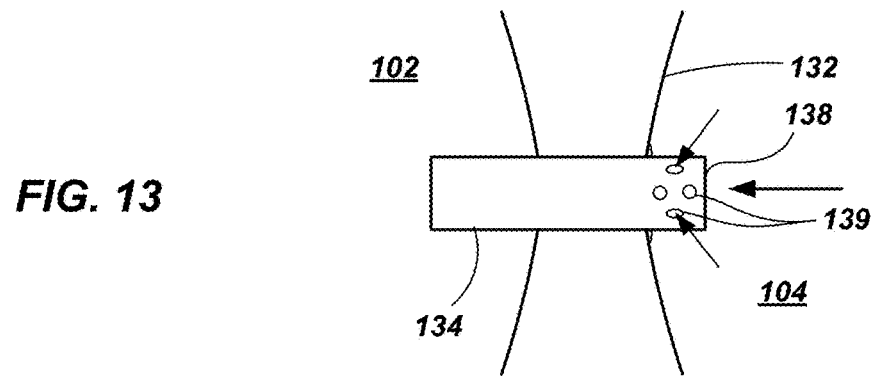
FIG. 13 is a component utilized in association with a ventricular assist device in accordance with another embodiment of the present invention.
Figure 14:
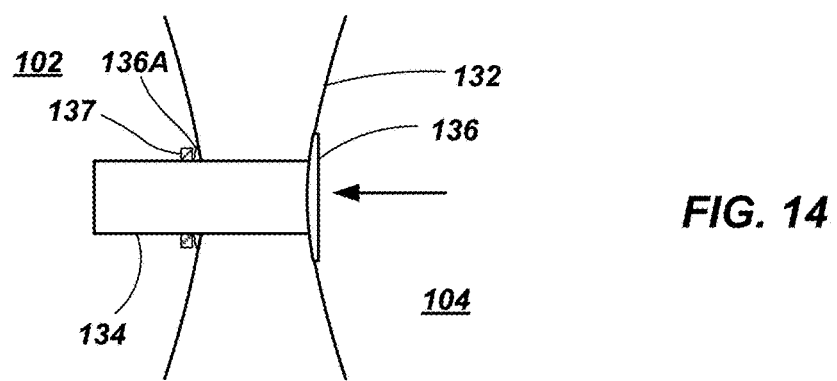
FIG. 14 is a component utilized in association with a ventricular assist device in accordance with an embodiment of the present invention.

It is noted, briefly, that other configurations of an anastomosis device 134 may be utilized. For example, it is contemplated that a portion of the anastomosis device 134 may protrude into the left atrium such as shown in FIG. 13. In such a case, an opening on the end 138, as well as lateral openings 139 may be used to draw blood from the left atrium 104. Again, such a structure enables blood to be drawn from the left atrium 104 with a relatively reduced level of pressure as compared to what is known as a reentrant connection where, for example, the end of the device protrudes into the left atrium and blood is drawn only through the opening at the end 138. As shown in FIG. 14, coupling of the anastomosis device may include positioning a grommet or a biasing member 137 (such as a member made of foam, elastomer, or other resilient material) against a shoulder 136A positioned on the right atrial side of the septum 132. The biasing member 137 may be used to effect a tighter fit of the anastomosis device 134 within the septum 132.

In one embodiment, the anastomosis device grommet 137 may be configured of a porous material to promote tissue in-growth and more securely connect the anastomosis device 134 to the septal tissue. Such materials might include, for example, foam, sintered titanium, porous tantalum, porous polytetrafluoroethylene (PTFE) or other porous material.

Figure 4:
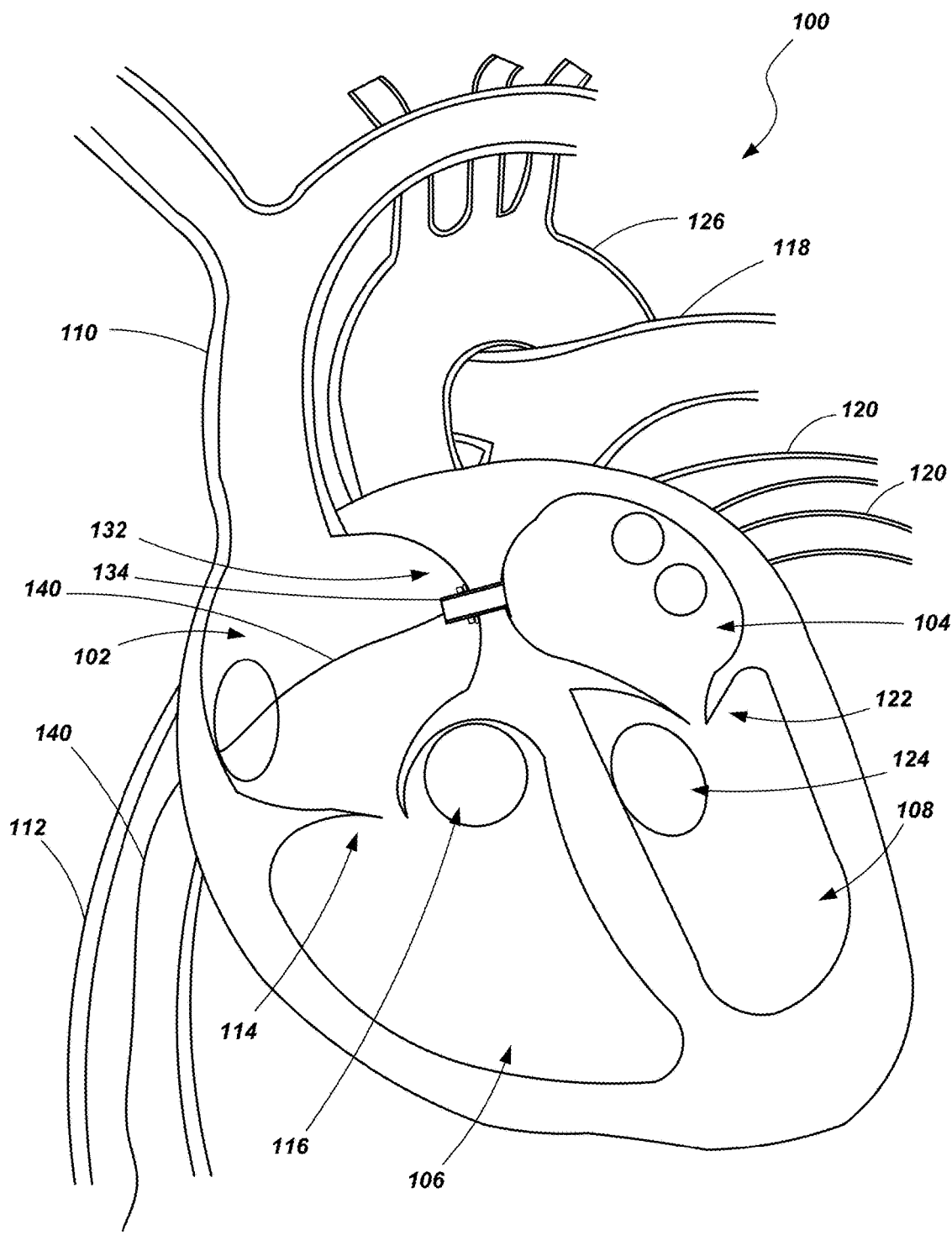

Referring to both FIGS. 3 and 4, as the catheter 130 is withdrawn, a filament member 140 remains with an end attached to the anastomosis device 134. The filament member 140 may include, for example, a strand of fibrous material, a braided member, a polymeric material a suturing material, or even a slender flexible wire. The filament member 140 may also be formed of a material, or include markers formed therein, that is (are) detectable by various imaging techniques to verify its position within the heart and veins. Examples of materials that may be used to form the filament that provide radio opacity include, but are not limited to, a wire made from tantalum, tantalum-tungsten alloy, platinum, platinum-iridium and stainless steel. Additionally, a wire may be coated with a polymer (e.g., nylon, urethane, PTFE, expanded PTFE or some polymer). When the catheter 130 is withdrawn, the filament member 140 remains attached to the anastomosis device 134 and may have a portion extending through the inferior vena cava 112 and, possibly, through other veins. In one embodiment, the filament may extend all the way through the access point, such as through an access point for a femoral vein.

Figure 5:
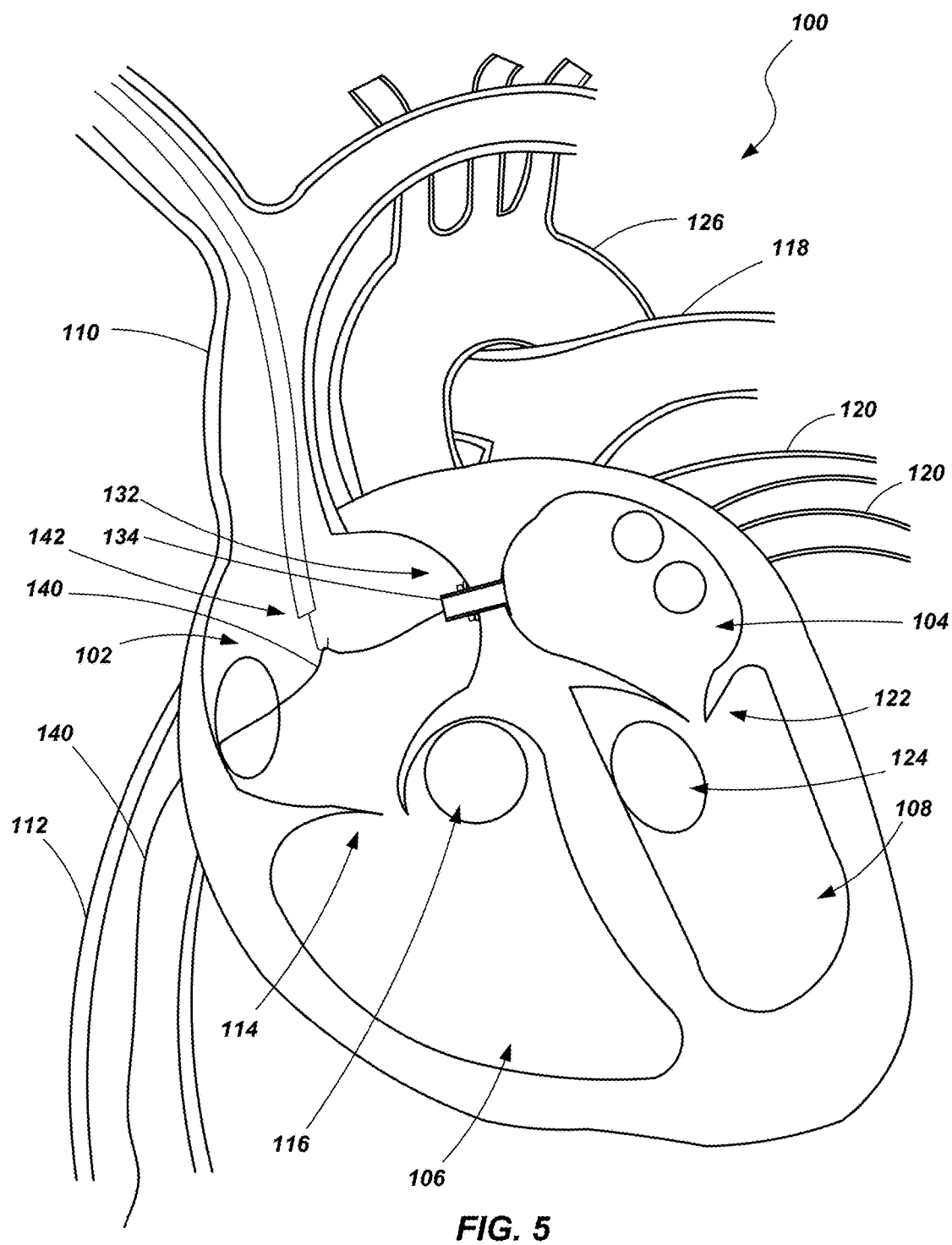
Figure 6:
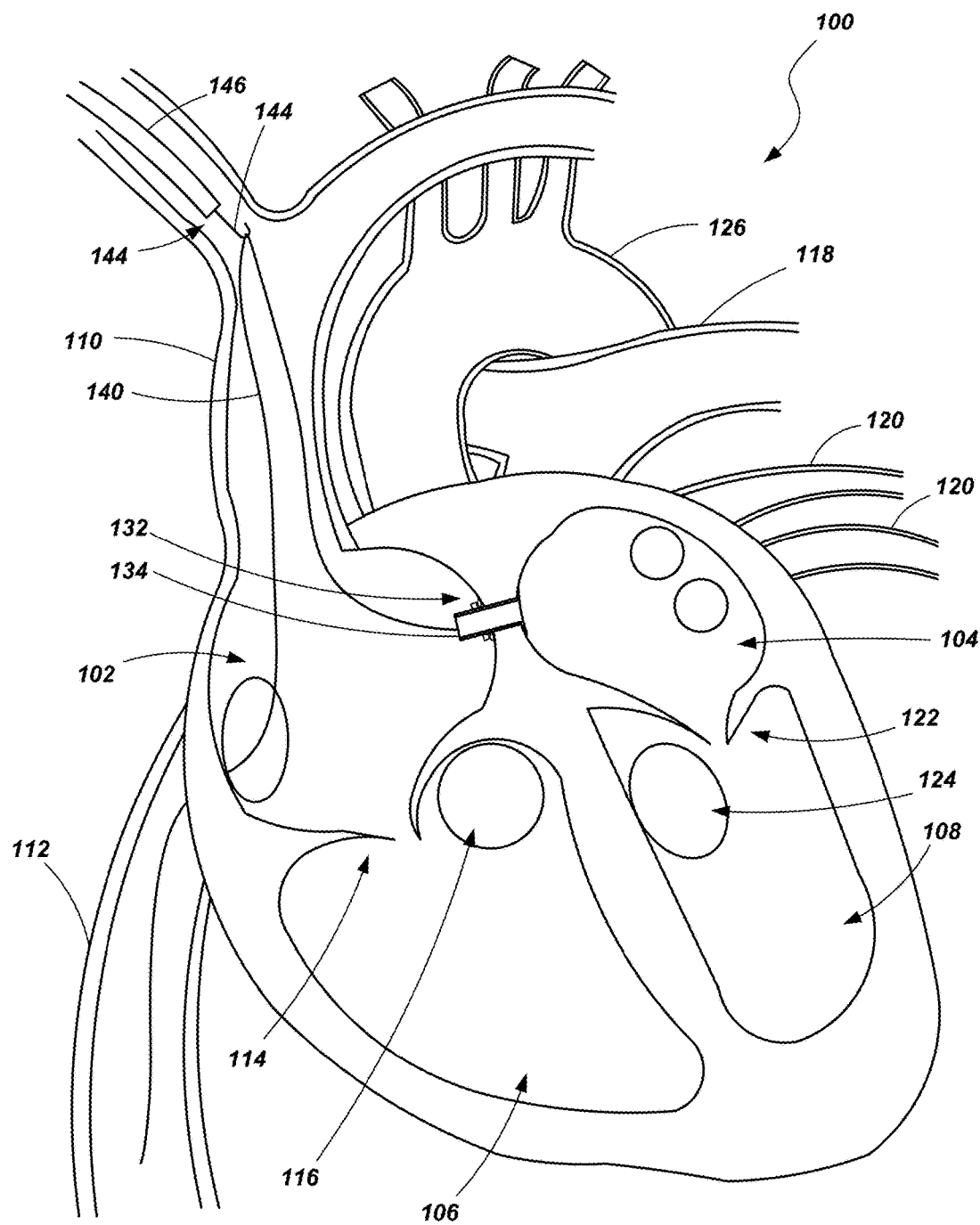
Figure 7:
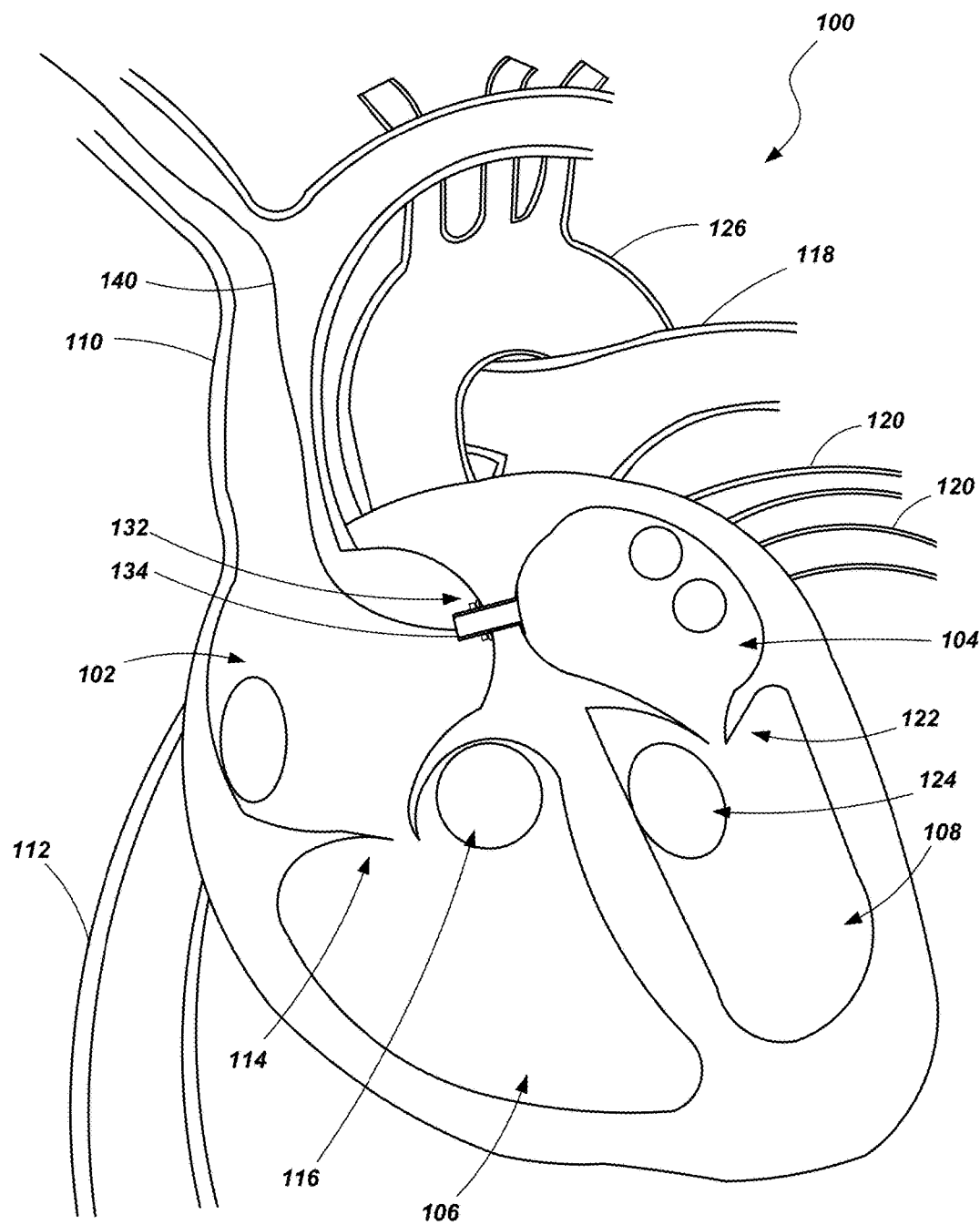

Referring to FIG. 5, a snare device 142 may be introduced into the right atrium 102 through the superior vena cava 110, such as by way of a jugular vein or the subclavian vein. The snare device 142 may be used to snare or grasp a portion of the filament member 140 disposed within the right atrium 102. Once the snare device 142 has grasped a portion of the filament member 140, the snare device 142 may be withdrawn from the right atrium 102 and then back through the superior vena cava 110. While not specifically shown, it is noted that the tip 144 of the snare device 140 may be positionable relative to an associated catheter housing 146 such that, while the snare device 140 is being deployed and withdrawn, it does not damage the tissue of the heart or veins to which the snare device 140 is exposed. As shown in FIGS. 6 and 7, as the snare device 142 is withdrawn, the filament member 140 is pulled up through the superior vena cava 110 and through any other vein (e.g., the jugular vein or the subclavian vein) which was used by the snare device 142 in gaining access to the right atrium 102.

Figure 8:
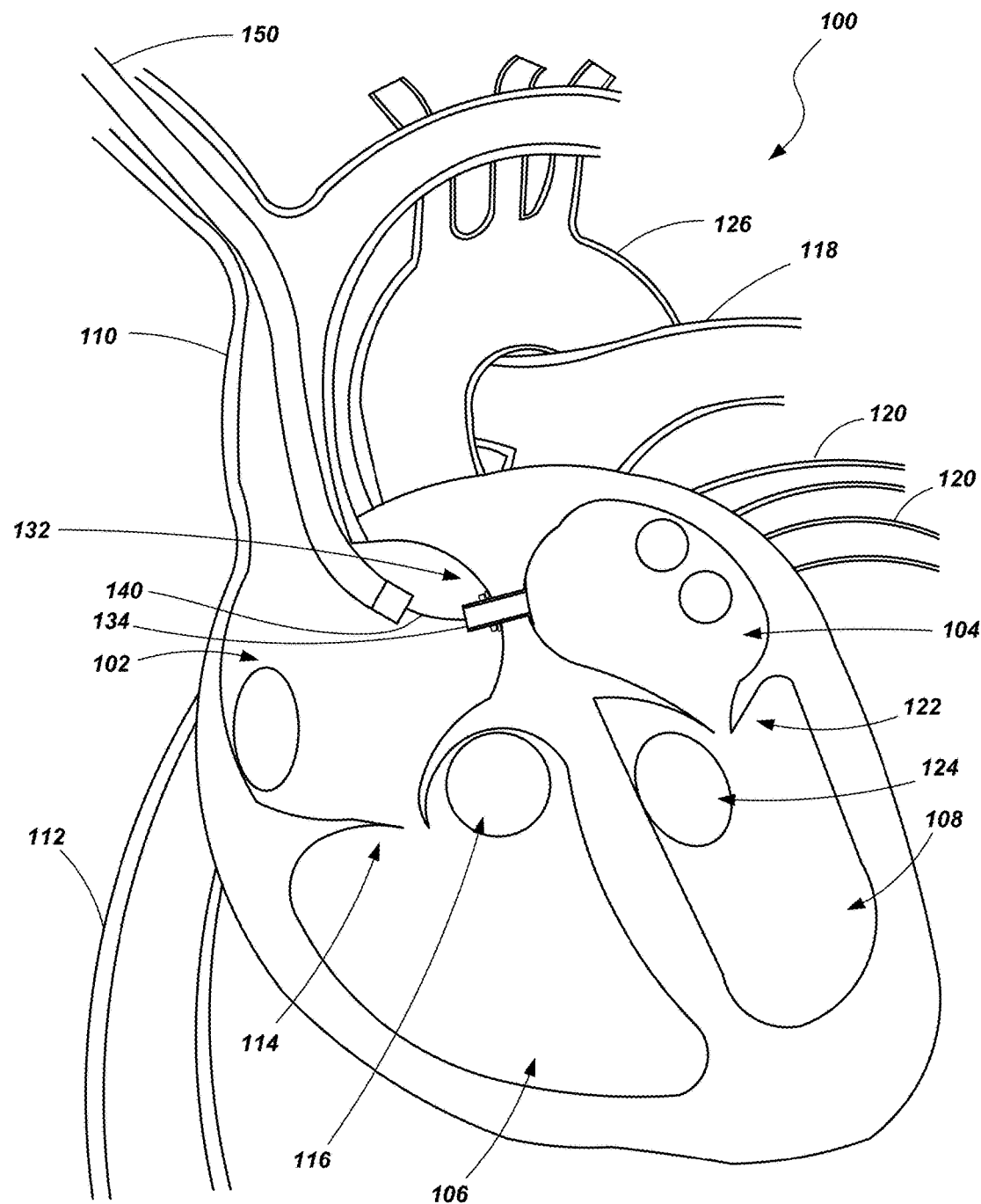
Figure 9:
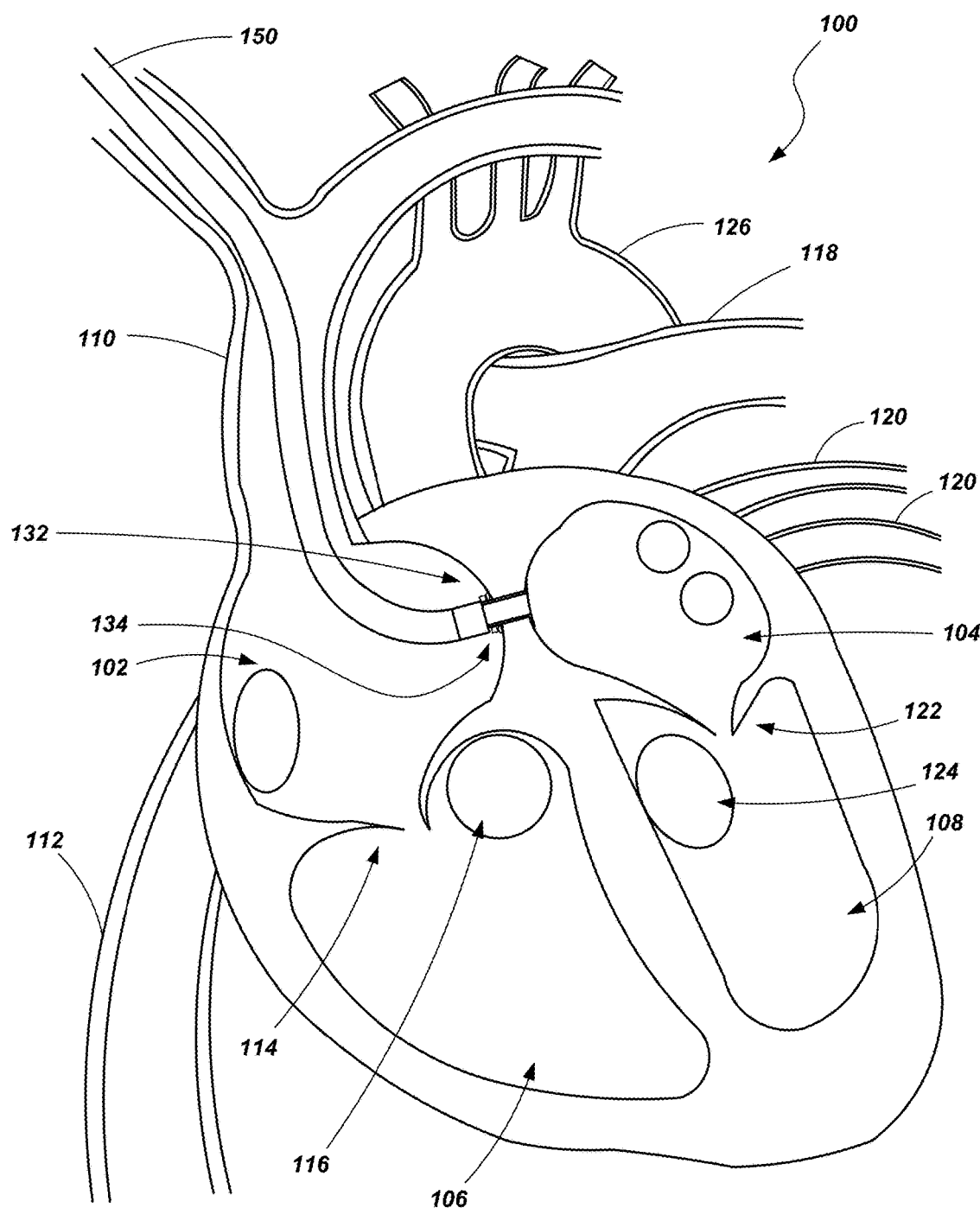

Referring to FIG. 8, a conduit 150 may be inserted into the right atrium 102, using the filament member 140 as a guide to follow the same path that was used by the snare device 142. FIG. 9 shows the conduit 150 coupled with the anastomosis device 134 creating a flow path for oxygenated blood from the left atrium 104, through the right atrium 102 (via the anastomosis device 134), through the superior vena cava 110 and through another vein such as the jugular or subclavian vein. The conduit 150 may include appropriately sized tubing or other material configured to be compatible with human tissue and to provide a fluid flow path for oxygenated blood from the left atrium 104 of the heart 100.

Figure 10:
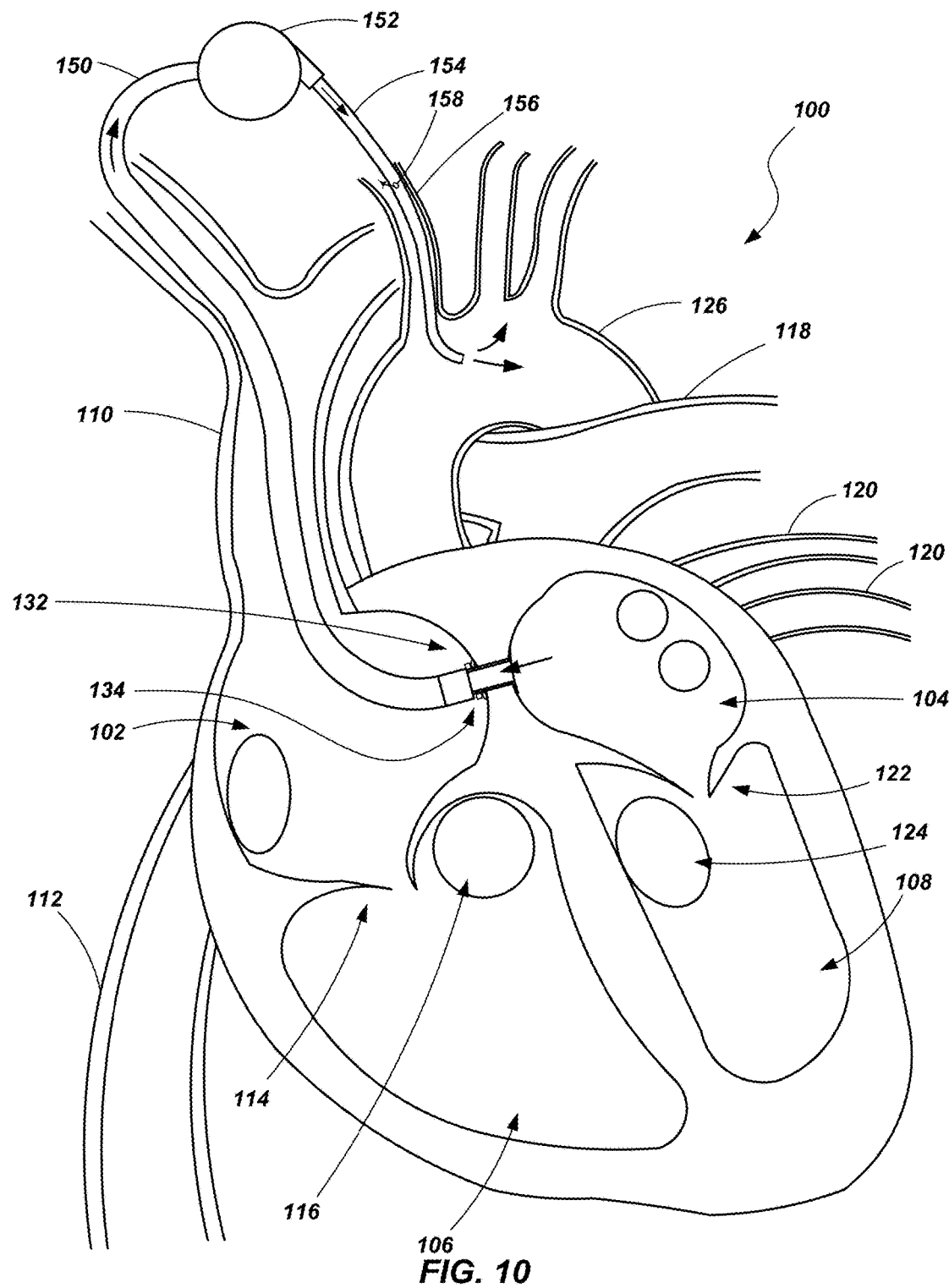

Referring to FIG. 10, the conduit 150 is coupled to a pumping device 152 which, in one embodiment, may be located external to the patient's body. A return conduit 154 is also coupled with the pumping device 152. The return conduit 154 is inserted into an artery to return the oxygenated blood to the circulatory system. For example, an outlet end of the return conduit 154 may be disposed in the aorta 126. The return conduit 154 may be routed, for example, through a brachial artery 156, although other appropriate routes may be utilized including a carotid artery. For example, the return conduit 154 may be routed to return flow to the left subclavian artery. In another embodiment, the return conduit 154 may be routed through the left subclavian artery and into the aortic arch, directing flow of blood downstream to prevent possible thrombi from entering, for example, the brachiocephalic artery or the left common carotid artery and traveling to the brain.

It is noted that, in some instances when the return conduit 154 is of a size that may obstruct or otherwise limit the flow of blood through the artery in which it is disposed (e.g., the brachial artery 156), one or more openings 158 may be formed within the return conduit 154 at upstream locations so that blood flow may be maintained within the associated artery hosting the return conduit 154.

In one example, the pumping device 152 may include a pump similar to a pump offered by Cardiac Assist, Inc. under the mark of TandemHeart®. The TandemHeart® pump is capable of pumping up to 5.0 liters per minute (lpm) when used percutaneously such as with the presently described system.

Figure 11:
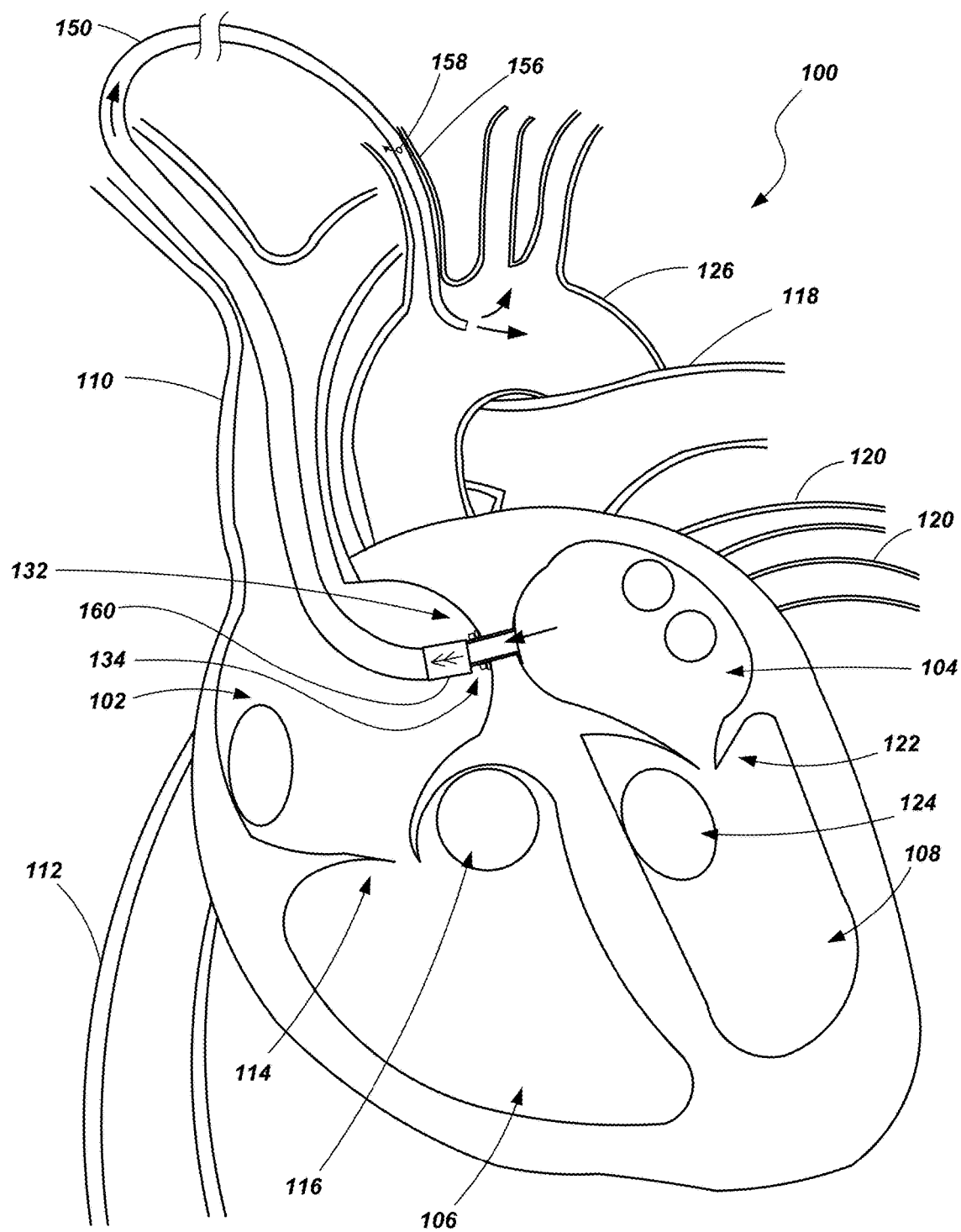

Referring briefly to FIG. 11, in another embodiment, the conduit 150 may extend from the right atrium 102 until it is returned into the aorta 126, such as through a brachial artery 156 or other route. A pumping device 160 is located within the right atrium 102 and coupled between the anastomosis device 134 and the conduit 150 effectively placing the pumping action at the septum 132. By locating the pumping device 160 at the septum 132, the oxygenated blood is subjected to less of a "vacuum" force and less head may be required. In other embodiments, the pumping device 160 may be located in the left atrium 104, the right ventricle 106 or the left ventricle 108. In such a case, wires or other transmission lines may also be feed through the superior vena cava 110 into the heart 100 to provide power to, and control of, the pumping device 160. In one embodiment, such wires may extend along side the conduit 150. In another embodiment, the wires may extend through a separate and distinct lumen formed within the conduit 150 or be contained within the wall of the conduit 150.

One example of a pump that may be placed in the right atrium (or even in one of the veins leading to the right atrium 102) is the pump utilized by Abiomed, Inc. with the product offered under the trademark Impella™. Of course, other suitable pumps, such as the above described TandemHeart® pump, may also be utilized.

In either of the embodiments shown in FIG. 10 or 11, oxygenated blood is drawn from the left atrium 104, through the anastomosis device 134, through the conduit 150 which passes through the superior vena cava and other veins such as the jugular or the subclavian, and is then returned to the aorta 126 through the return conduit 154 (or via the conduit itself in FIG. 11) which passes through an artery such as a brachial artery or a carotid artery.

One advantage of the described systems and methods includes the placement of the conduits. By routing the conduits (e.g., 150 and 154) through the superior vena cava 110 and arteries such as a brachial artery or a carotid artery, the system is easier to maintain and infections are less likely to occur. Often, when conduits are routed through the femoral veins or arteries for ventricular assist devices, infection is a likely complication. Additionally, use of a filament to guide the conduit 150 to the septum 134 is advantageous as it may be difficult to steer and access a structure to such a location via the superior vena cava independent of such a guide structure.

Figure 15:
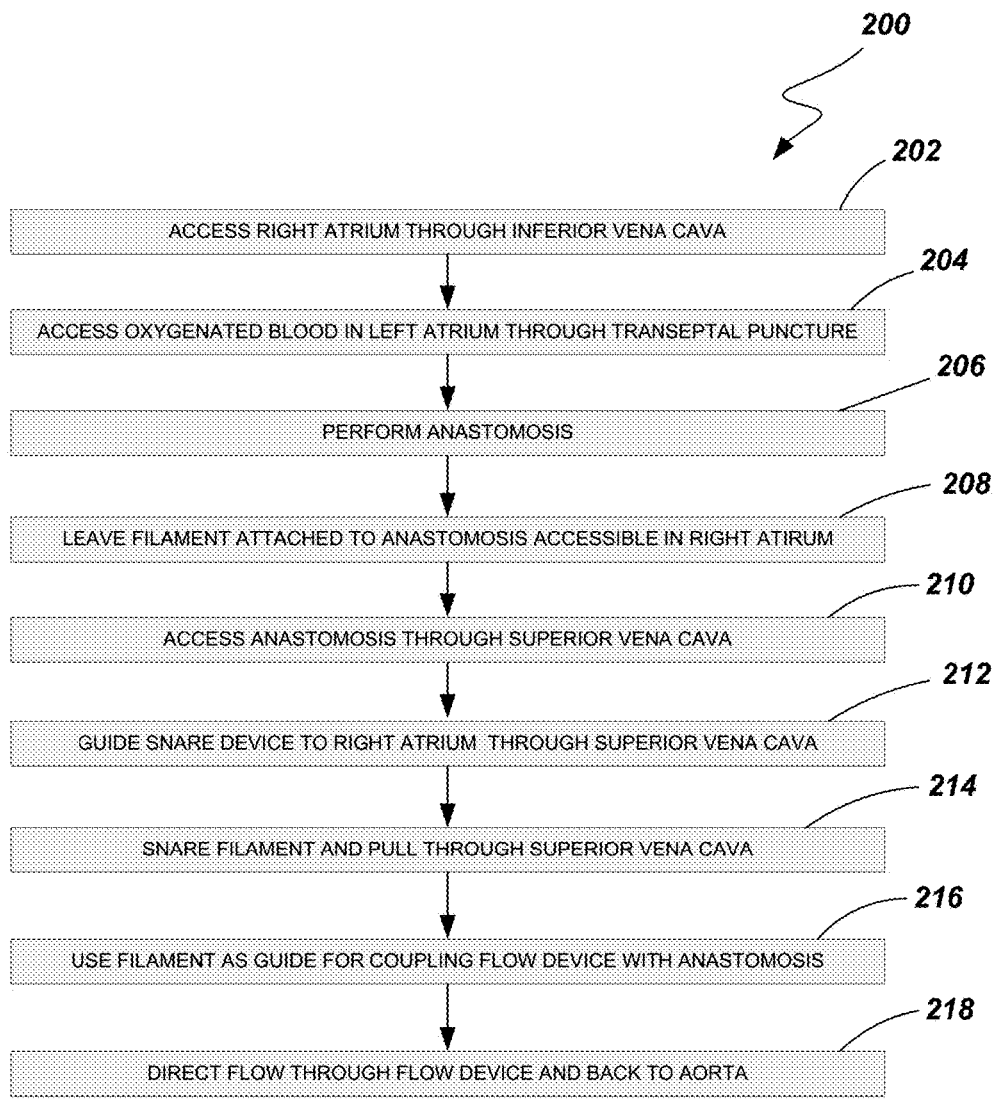
FIG. 15 is a block diagram showing various acts in one example of percutaneously gaining access to oxygenated blood and pumping such blood to other arterial regions of the vascular system via an LVAD, according to an embodiment of the present invention.

Referring now to FIG. 15, various acts of a method 200 according to the present invention are shown. As described above with respect to FIGS. 2-11, the method provides access to oxygenated blood with an anastomosis device and includes pumping such oxygenated blood to other arterial regions of the vascular system. Such access to oxygenated blood is first initiated by percutaneous access to the femoral vein. As depicted at 202, a catheter may be inserted through the femoral access point up through the inferior vena cava into the right atrium. As previously noted, the catheter may be guided with the assistance of, for example, fluoroscopic and/or ultrasound imaging. As depicted at 204, a trans-septal puncture may be performed at a location in the atrial septum accessing oxygenated blood contained in the left atrium. As shown at 206, anastomosis can be performed with a catheter-based device which, in one embodiment, attaches only to the right atrial side of the atrial septum preventing potential thrombus formation or securement issues of an in-flow cannula protruding through the septal wall, or into the left atrium. Further, by attaching an anastomosis device to the right atrial side of the atrial septum, there is far less resistance to flow of the blood from the left atrium than that of an in-flow cannula protruding through the septal wall and into the left atrium.

As set forth at 208, after the anastomosis is performed, the catheter system can be withdrawn from the right atrium, from which a filament remains connected to the anastomosis device. As shown at 210, the anastomosis device is accessed by percutaneous access through the venous system, such as the subclavian or jugular vein. An intra-vascular snare device can be inserted through this subclavian or jugular vein access point and guided into the right atrium, as set forth at 212. The snare device can then be used to snare the filament that is attached to the anastomosis device and to exteriorize it through the access point, as set forth at 214.

As set forth at 216, the filament can then be used as a guide to insert a conduit, such as the in-flow catheter of a VAD pump, through the access point and up to the anastomosis device where it is attached thus providing access to oxygenated blood to the VAD pump. As set forth at 218, a conduit, such as an out-flow catheter of the pump, is percutaneously attached to a brachial artery or a carotid artery or even the aorta via another anastomosis device or another type of connection. In one embodiment, this additional anastomosis device can be similar to that used for connection of the in-flow catheter to the atrial septum. Further, it is contemplated that the LVAD can be disposed externally or internally. In one embodiment, the LVAD can be disposed in the chest, external the ribs or thoracic cavity, in the soft tissue, similar to a pace-maker.

Having considered the above examples, it is further noted that a similar procedure may be performed in the ventricles 106 and 108 of the heart 100 rather than the atria 102 and 104. For example, access to the right ventricle 106 may be obtained by first accessing the right atrium 102, as described above, and then passing a catheter 130 or other device through the tricuspid valve 114 into the right ventricle 106. The septum between the right and left ventricles 106 and 108 may then be punctured to access oxygenated blood in the left ventricle 108. An anastomosis device 134 may then be positioned in the septum between the right and left ventricles and the procedure may follow as outlined above, except that access to oxygenated blood will be through the anastomosis device in the right ventricle 106 rather than in the right atrium 102.

Additionally, while the description above has been set forth as performing the anastomosis procedure by access through the inferior vena cava 112, it is noted that access to the right atrium 102 or right ventricle via the inferior vena cava 112 may simply be to attach a filament 140 to, for example, the septum (either between atria 102 and 104 or between ventricles 106 and 108). The filament 140 may then be used to guide a conduit or other cannula to the septum, the conduit or cannula having an anastomosis device to be installed in the septum.

It is further noted that various acts or portions of the described embodiment may be used independent of others. Thus, the present invention contemplates transeptal access to the left side of the heart for use in other procedures, or in procedures where the oxygenated blood is routed differently than described in the example embodiments set forth above.

Figure 16:
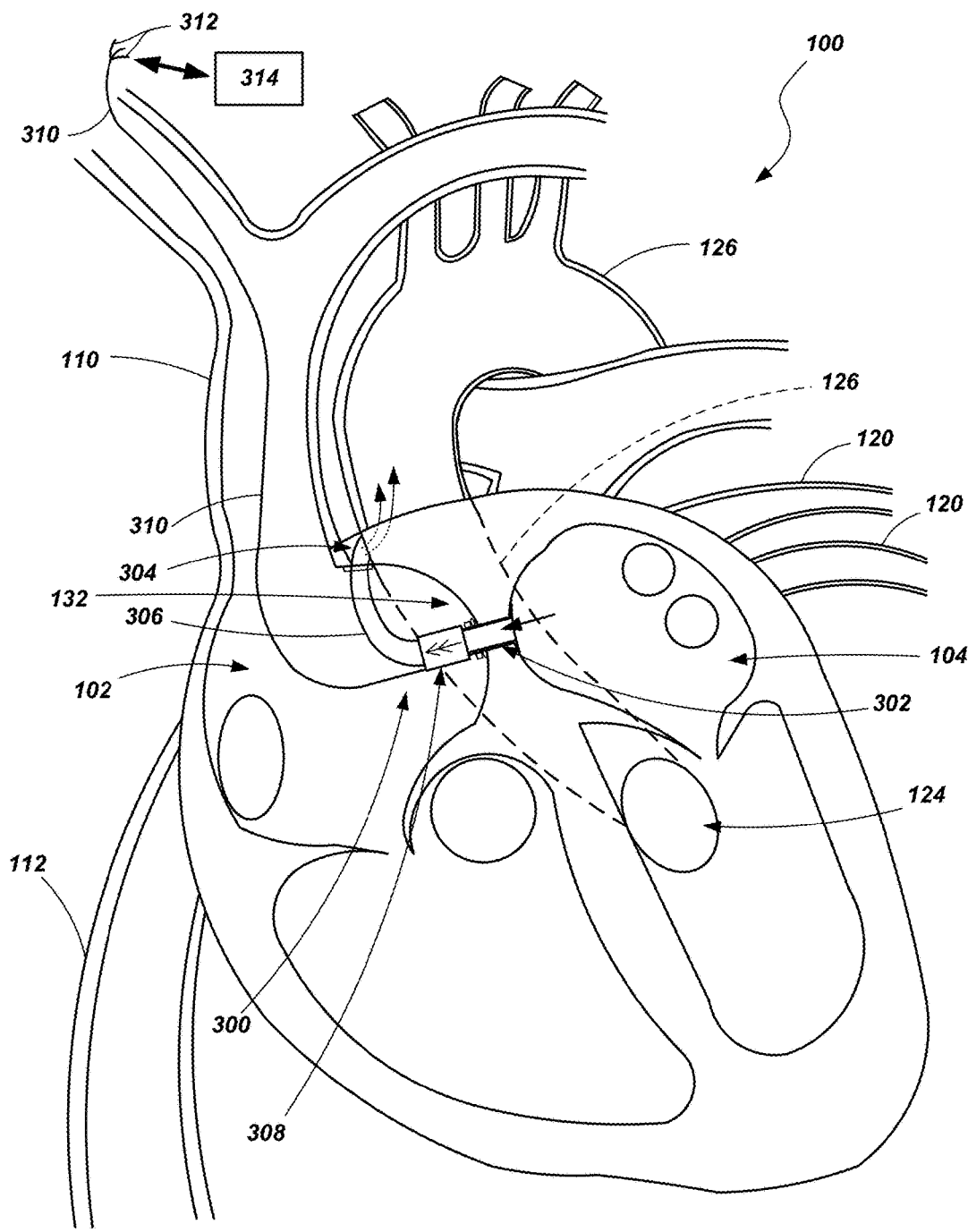
FIG. 16 is a simplified, cross-sectional view of a human heart depicting another embodiment of a VAD system and method, according to the present invention.

With respect to FIG. 16, in another embodiment, a VAD system 300 and method is shown. In particular, the VAD system 300 may include a first anastomosis device 302, a second anastomosis device 304, one or more conduits 306 and a pumping device 308 with a filament 310 extending from the pumping device 308. The first anastomosis device 302 can be secured in the septum 132 between the right atrium 102 and the left atrium 104, as previously set forth, and sized and configured to pull arterial blood or oxygenated blood from the left atrium 104. The second anastomosis device 304 may be secured and positioned from the right atrium 102 directly to the aorta 126, where the aorta 126 extends adjacently along the right atrium 102. The pumping device 308 may be positioned between or at the first anastomosis device 302 and the second anastomosis device 304. The conduit 306 also may extend between the first anastomosis device 302 and the second anastomosis device 304 to act as a flow canal for the arterial blood being pumped therethrough. Such conduit 306 can be a flexible material, such as woven polyester, polyurethane, ePTFE, or PVC, or any suitable biocompatible material. With this arrangement, arterial blood may be pumped directly from the left atrium 104 into the aorta 126 with the VAD system 300 positioned within the right atrium 102. The pumping device 308 can include a filament 310 extending therefrom that can be snared, similar to the filament of the previous embodiments, to be pulled through the superior vena cava 110 and exposed in the upper regions of the body, such as from the jugular or subclavian vein. In another embodiment, the filament 310 can extend through the femoral vein to be exposed at an access point at the lower region of the body. Such filament can include multiple electrical wires 312 sized and configured to operatively connect to a controller 314 to, thereby, facilitate the power and control of the pumping device 308. In this manner, the flow rate and characteristics of the arterial blood being pumped from the left atrium 104 into the aorta 126 can be controlled remotely with the pumping device 308 adjacent to the left atrium with a limited flow path length required for the pumping device to pump the arterial blood. Such limited distance for the arterial blood to move through the conduit 306 in the right atrium 102 directly to the aorta 126 maximizes the efficiency of the pumping device 308 and limits the work required for the pumping device 308. In another embodiment, it is contemplated that the pumping device 308 can be powered and controlled wirelessly, in addition to or instead of the filament 310. It should be noted that the anastomosis device positioned into the aorta 126 is intended to be downstream of the aortic valve 124, as depicted.

The VAD system 300 of this embodiment may be implanted in the right atrium 102 by first performing an anastomosis with the first anastomosis device 302 in the septum 132 for pulling arterial blood from the left atrium 104. The first anastomosis device 302 can include a line (not shown) left loose therefrom at this stage. Next, another anastomosis may be made from the right atrium 102 into the aorta 126, downstream of the aortic valve 124. The second anastomosis device 304 can then be positioned and placed within the anastomosis to the aorta 126. The pumping device 308 and conduit 306 can then be delivered through the inferior vena cava 112, via the femoral vein, and into the right atrium 102. For example, the pumping device 308 can be secured to an end of the first anastomosis device 302 by tracking the line extending from the first anastomosis device 302. The conduit 306 extending from the pumping device 308 can then be positioned over an end of the second anastomosis device 304. In another embodiment, the pumping device 308 and the conduit 306 may be integrated with the first anastomosis device 302, such that delivery of first anastomosis device 302 includes delivery of the pumping device 308 and conduit 306. In either case, the filament 310, that extends from the pumping device 308, may then be snared and pulled through the superior vena cava 110 and exposed from, for example, the subclavean vein or jugular vein. The physician can then interconnect the controller 314 to the multiple wires 312 of the filament 310, exposed on the patient. The controller 314 can include controls for powering the pump and controlling the flow characteristics of the arterial blood being pumped through the VAD system 300.

The above noted VAD system 300 may be implanted employing multiple separate catheter systems each sized and configured to perform their distinct function of delivering, for example, the first anastomosis device 302, the second anastomosis device 304, and the pumping device 308 and conduit 306. In another embodiment, the VAD system 300 can be delivered employing a single large catheter with one or more smaller in diameter catheters or various delivery elements within the large catheter. In one embodiment, the smaller diameter catheters may be substantially concentric with the large catheter. Further, it should be noted that the procedure for implanting the VAD system 300 of this embodiment may include performing the anastomosis to the aorta 126 from the right atrium 102 first and then performing the anastomosis between the right and left atria. As known to one of ordinary skill in the art, the one or more delivery systems may also include a dilator and stylet or needle to perform the anastomosis procedures. Further, the first anastomosis device 302 and the second anastomosis device 304 of this embodiment can be similar to the embodiments of the anastomosis device set forth previously, as depicted in FIGS. 12 through 14.

Figure 17:
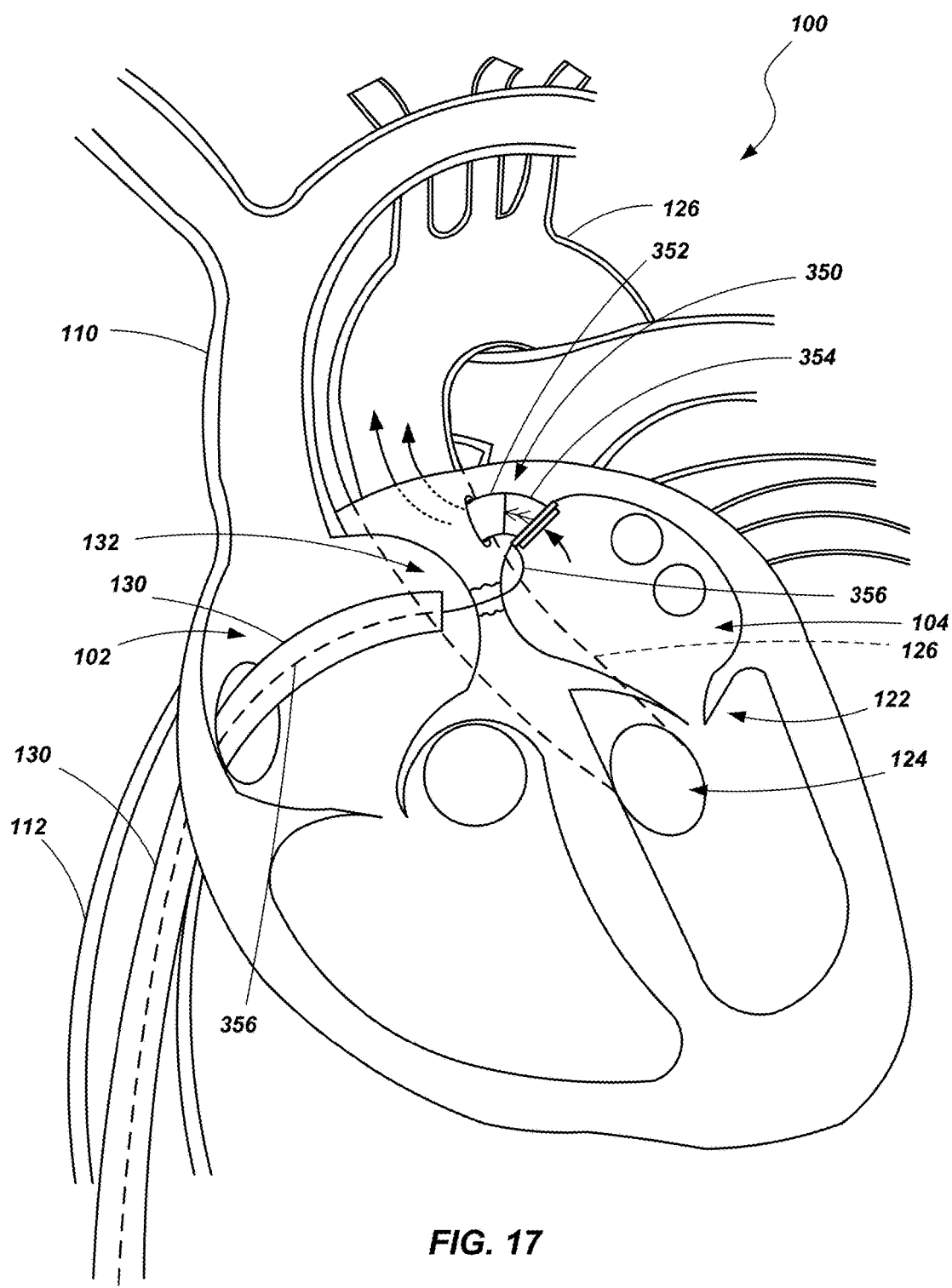
FIG. 17 is a simplified, cross-sectional view of a human heart depicting another embodiment of a VAD system and method, according to the present invention.

As depicted in FIG. 17, another embodiment of a VAD system 350 and method is shown. The VAD system 350 may include an anastomosis device 352, a pumping device 354 and a filament 356 extending from the pumping device 354. In this embodiment, the anastomosis may be formed within the left atrium wall at a location adjacent the aorta or, otherwise, between the left atrium 104 and aorta 126. The anastomosis device 352 may include a conduit which may be placed within the anastomosis to facilitate a direct communication from the left atrium 104 to the aorta 126. For example, in one embodiment, the anastomosis device 352 can include the pumping device 354 positioned therewith, such as extending into the left atrium to push oxygenated blood through the anastomosis device 352, or positioned within a bore or conduit of the anastomosis device 352 itself. The VAD system 350 can include a filament 356, the filament 356 extending from the pumping device 354. As in the previous embodiment, the filament 356 can include multiple wires configured to power and control the pumping device 354 from a location remote of the pumping device 354, such as at a location exposed on the patient.

The method of delivering the VAD system 350 of this embodiment can be employed utilizing any known method in the art for accessing the left atrium 104 with a catheter, or any other known method for accessing the left atrium 104. For example, the left atrium 104 can be accessed by tracking a catheter 130 through the inferior vena cava, via the femoral vein, into the right atrium 102, and then puncturing the septum 132 in the right atrium 102 to gain access into the left atrium 104. The anastomosis can then be made at any suitable location in the left atrium wall that is adjacent the aorta 126. Once the anastomosis is made, the anastomosis device 352, with the integrated pumping device 354, may then be deployed from the catheter 130 and implanted within the wall between the left atrium 104 and the aorta 126. In one embodiment, portions of the VAD system 350 may extend beyond the wall, e.g., within the left atrium. The catheter 130 may then be withdrawn from the left atrium 104 into the right atrium 102, tracking along the filament 356 that extends from the pumping device 354. Once the catheter 130 is withdrawn from the femoral vein, the filament may be exposed at the access point in the femoral vein. The physician may then attach a controller to the multiple wires of the filament (not shown). If preferred, the filament 356 may be snared, as set forth in previous embodiments, within the right atrium 102 and pulled through the superior vena cava 110 and pulled out through an access point, at, for example, the subclavian vein or at any suitable location at the upper region of the body. The physician can then attach a controller to the multiple wires of the filament 356 for remotely controlling the pumping device 354 of the VAD system 350, similar to that depicted in the previous embodiment. Further, the anastomosis device 352 of this embodiment may be similar to the structure and features of the embodiments depicted in FIGS. 12 through 14 or any other embodiments set forth herein.

In another embodiment, the VAD system 350 depicted in FIG. 17 may be implanted surgically and/or in part with an endovascular procedure. In this embodiment, the filament 356 may extend from the pumping device 354 subcutaneously therefrom to be exposed at an upper region of the body of the patient, such as in the chest or shoulder region.

Figure 18:
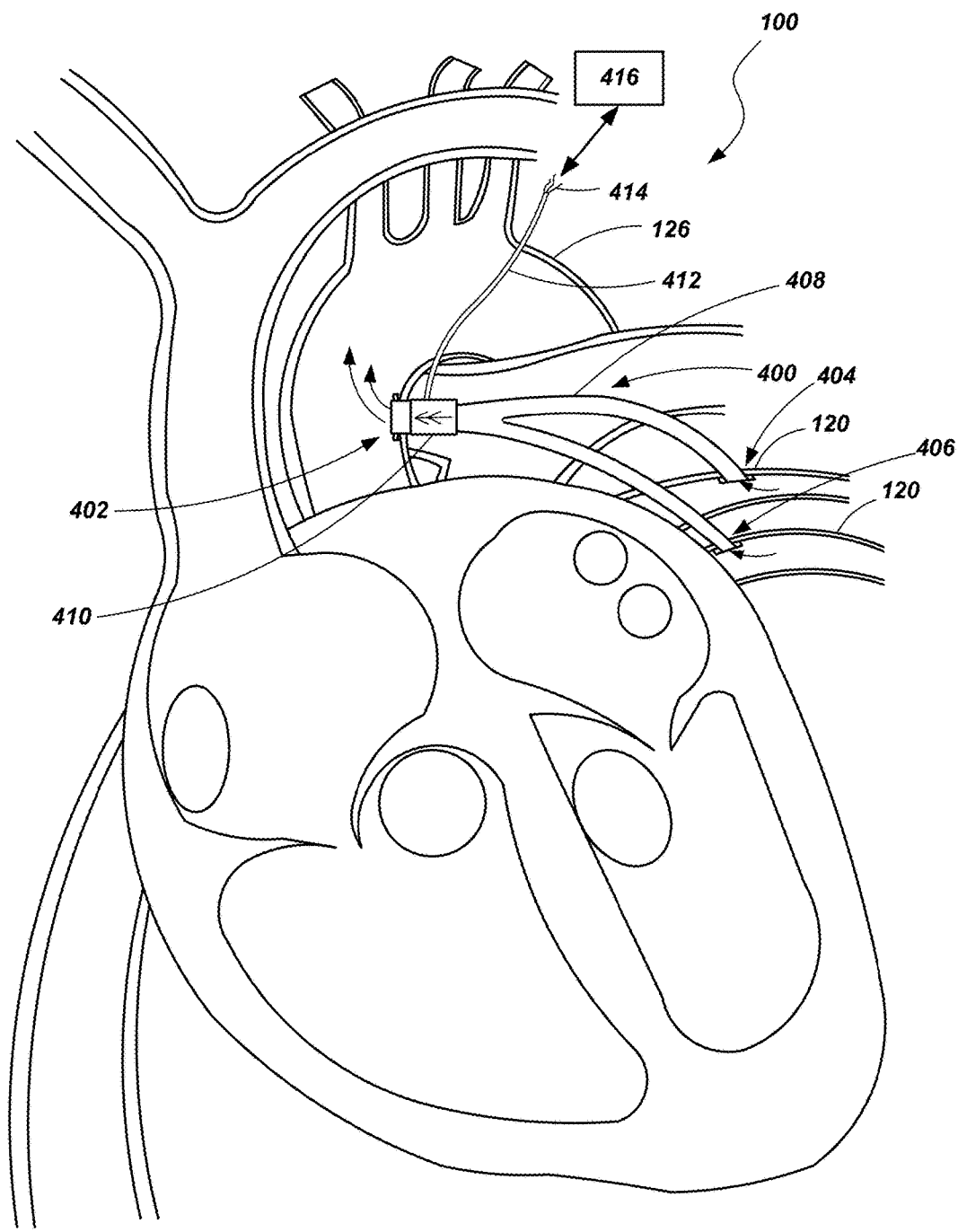
FIG. 18 is a simplified, cross-sectional view of a human heart depicting another embodiment of a VAD system and method, according to the present invention.

Referring now to FIG. 18, in another embodiment, a VAD system 400 configured to be implanted surgically is provided. The VAD system 400 may include a graft with a pumping device disposed therein between the aorta and one or more pulmonary veins. More specifically, the VAD system 400 may include a first anastomosis device 402, a second anastomosis device 404, a conduit 408, a pumping device 410 and a filament 412. In one embodiment, the first anastomosis device 402 may be positioned and secured in the aorta 126, via an anastomosis procedure, and the second anastomosis device 404 may be positioned and secured in the pulmonary vein 120, via another anastomosis procedure, with conduit 408 extending therebetween. The pumping device 410 may be disposed at or between the first anastomosis device 402 and the second anastomosis device 404. The filament 412 may extend from the pumping device 410, subcutaneously, to be exposed at the upper region of the patients body, such as in the chest or shoulder region. The filament 412, as in previous embodiments, includes multiple lead wires 414 configured to be interconnected to a controller 416 to power and control the pumping device 410. With this arrangement, the pumping device 410 can pull oxygenated blood from the pulmonary veins 120 directly to the aorta 126 to assist the heart 100. In another embodiment, a third anastomosis device 406 may be employed in another pulmonary vein 120, from which another flow path with conduit 408 can extend to the aorta 126 through, for example, the first anastomosis device 402 such that the conduit 408 may include a bifurcated arrangement, as depicted. Further, any one of the first anastomosis device 402, the second anastomosis device 404, and the third anastomosis device 406 may include structure and features similar to the embodiments set forth with respect to FIGS. 12 through 14, or similar to any of the other embodiments of an anastomosis device described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A system to assist a left ventricle of a heart, the system comprising:
   an anastomosis device coupled to a septum between two chambers of the heart, the anastomosis device configured to provide a pathway between the two chambers;
   a flow path including at least one conduit and configured to flow oxygenated blood from at least one of the left atrium and the left ventricle, through the anastomosis device, through the superior vena cava and back to an artery;
   a pumping device coupled with the at least one conduit; and
   a filament coupled to the anastomosis device, wherein the filament exhibits sufficient length to extend from the anastomosis device through the superior vena cava and to an access point associated with at least one of a jugular vein and a subclavian vein;
   wherein the filament comprises multiple wires configured to facilitate power and control of the pumping device via a controller.

2. The system of claim 1, wherein the at least one conduit includes:
   a first conduit coupled with the anastomosis device and extending through the superior vena cava; and
   a second conduit extending through one of a brachial artery, a carotid artery, a subclavian artery, and a axillary artery and having an outlet disposed in an aortic artery.

3. The system of claim 2, wherein the pumping device is coupled between the first conduit and the second conduit.

4. The system of claim 1, wherein the pumping device is coupled between the anastomosis device and the at least one conduit.

5. The system of claim 1, wherein the pumping device is coupled directly to the anastomosis device.

6. The system of claim 1, wherein the anastomosis device is shaped and configured to be substantially flush with a left wall of the septum.

7. The system of claim 1, wherein a portion of the anastomosis device protrudes past a left wall of the septum, and wherein the portion includes a plurality of openings therein.

8. The system of claim 1, wherein the anastomosis device comprises a tubular structure extending between a first end and a second end, the anastomosis device having a shoulder extending laterally from the first end of the tubular structure such that the shoulder is positioned substantially flush with a left atrium wall at the septum and the second end extending into the right atrium.

9. The system of claim 8, wherein the at least one conduit is coupled directly to the second end of the tubular structure.

10. The system of claim 1, wherein the at least one conduit comprises a lumen, wherein the filament extends through the lumen of the at least one conduit.

11. A kit for percutaneous connection of an assist device to a heart, the kit comprising:
    an anastomosis device sized and configured to be installed in an opening of one of an atrial septum and a ventricular septum, the anastomosis device including a tubular structure extending between a first end and a second end;
    a filament fixedly coupled to the anastomosis device; and
    a snare device sized and configured to access a chamber of the heart through a superior vena cava, the snare device also being configured to grasp the fixed filament and pull the filament through the superior vena cava;
    at least one conduit defining a lumen therethrough, one end of the at least one conduit sized and configured to be installed and coupled to the second end of the tubular structure of the anastomosis device; and
    a pumping device configured to be installed and coupled to the at least one conduit;
    wherein the filament comprises multiple wires configured to facilitate power and control of the pumping device via a controller.

12. The kit of claim 11, wherein the filament exhibits sufficient length to extend from the anastomosis device, when installed in the septum wall, through the superior vena cava and to an access point associated with at least one of a jugular vein and a subclavian vein.

13. The kit of claim 11, wherein the at least one conduit comprises a lumen, wherein the filament extends through the lumen of the at least one conduit.

14. The kit of claim 11, wherein the pumping device is sized to be positioned within the heart and adjacent the anastomosis device.

15. The kit of claim 12, wherein the pumping device is sized to be positioned adjacent the access point.

16. The kit of claim 11, further comprising a second anastomosis device configured to be coupled between the right atrium of the heart and the aorta.

* * * * *